(12) United States Patent
Sung et al.

(10) Patent No.: US 9,545,295 B2
(45) Date of Patent: Jan. 17, 2017

(54) NANO BUBBLE GENERATOR FOR CLEANING ROOT CANAL OF TOOTH AND DENTAL APPARATUS COMPRISING THE SAME

(71) Applicant: B&L BIOTECH, INC., Ansan-si, Gyeonggi-Do (KR)

(72) Inventors: JaeYong Sung, Seoul (KR); Taejun Bang, Wonju-si (KR); Inwhan Lee, Seoul (KR); Inje Cho, Seoul (KR); Gilhwan Sung, Seoul (KR); Seung Ki Baek, Seoul (KR)

(73) Assignee: B&L BIOTECH, INC., Ansan-si, Gyeonggi-do (KR)

( * ) Notice: Subject to any disclaimer, the term of this patent is extended or adjusted under 35 U.S.C. 154(b) by 272 days.

(21) Appl. No.: 14/340,549

(22) Filed: Jul. 24, 2014

(65) Prior Publication Data

US 2015/0030991 A1    Jan. 29, 2015

(30) Foreign Application Priority Data

Jul. 25, 2013 (KR) .......... 10-2013-0088163
Jul. 14, 2014 (KR) .......... 10-2014-0088346

(51) Int. Cl.
*A61C 17/02* (2006.01)
*A61C 17/20* (2006.01)
*A61C 5/02* (2006.01)

(52) U.S. Cl.
CPC ............ *A61C 17/20* (2013.01); *A61C 5/02* (2013.01); *A61C 17/02* (2013.01)

(58) Field of Classification Search
CPC ............ A61C 17/20; A61C 17/02; A61C 5/02
USPC .......... 433/80, 81, 86, 102, 119, 215
See application file for complete search history.

(56) References Cited

U.S. PATENT DOCUMENTS

| | | | | |
|---|---|---|---|---|
| 2010/0143861 | A1* | 6/2010 | Gharib | A61C 5/02 433/81 |
| 2011/0111365 | A1* | 5/2011 | Gharib | A61C 5/02 433/81 |
| 2012/0276497 | A1* | 11/2012 | Gharib | A61C 17/02 433/27 |
| 2015/0327963 | A1* | 11/2015 | Fregoso | A61C 3/00 433/29 |
| 2016/0095679 | A1* | 4/2016 | Khakpour | A61C 17/0202 433/81 |

FOREIGN PATENT DOCUMENTS

| | | |
|---|---|---|
| JP | 2013-126502 A | 6/2013 |
| KR | 10-2011-0118305 A | 10/2011 |
| KR | 20-0462769 Y1 | 9/2012 |
| KR | 10-2014-0028079 A | 3/2014 |

\* cited by examiner

*Primary Examiner* — Glenn Richman
(74) *Attorney, Agent, or Firm* — Novick, Kim & Lee, PLLC; Sang Ho Lee (57) ABSTRACT

Provided are a nano bubble generator for irrigating a root canal of a tooth and a dental device including the nano bubble generator. The nano bubble generator may include a generator configured to generate nano-scale bubbles within a fluid, a nozzle connected to the generator and configured to move the fluid containing bubbles that flows in from the generator and to apply the fluid at the end of the nozzle, and an ultrasonic portion disposed in the nozzle and configured to apply ultrasonic waves to the fluid containing the bubbles so that the bubbles are maintained in a distributed form.

5 Claims, 6 Drawing Sheets

NANO BUBBLE GENERATOR FOR CLEANING ROOT CANAL OF TOOTH AND DENTAL APPARATUS COMPRISING THE SAME

CROSS-REFERENCE TO RELATED APPLICATIONS

This application claims the priority benefit of Korean Patent Application No. 10-2013-0088163, filed on Jul. 25, 2013, and Korean Patent Application No. 10-2014-0088346, filed on Jul. 14, 2014 in the Korean Intellectual Property Office, the disclosures of which are incorporated herein by reference.

BACKGROUND

1. Field of the Invention

Embodiments of the present invention relate to a nano bubble generator for irrigating a root canal of a tooth and a dental device including the nano bubble generator, and more particularly, to a nano bubble generator for irrigating a root canal of a tooth that may spray nano-scale bubbles and a dental device including the nano bubble generator.

This work was supported by the Technological Innovation R&D Program (S2163003, Nanobubble Irrigation System) funded by Small and Medium Business Administration (SMBA, KOREA).

2. Description of the Related Art

A nerve treatment refers to a method that, when the dental pulp is infected due to bacteria of a cavity or becomes inflamed due to noxious stimulus, may completely remove and clean the infected tissues and dental pulp within a root canal of a tooth and then may fill a predetermined filling material in the corresponding space, thereby preventing bacteria from intruding into the root canal and helping the tooth becomes autonomously treated to be healthy.

In the recent times, such dental nerve treatment technology has been construed being very important and completely removing foreign substances from within the root canal is required for a success in the treatment. In particular, the inside of the root canal is small as a micro unit and contacts with the tissue cells of the gum. Accordingly, it may be significantly difficult to remove foreign substances from within the root canal.

A variety of methods for irrigating foreign substances present within the root canal may be employed, and may include, for example, a syringe-needle irrigation method, a manual dynamic irrigation method, a brush method, a sonic irrigation method, an ultrasonic irrigation method, and a laser-activity irrigation method. In this instance, the ultrasonic irrigation method is most preferred as the latest technology capable of irrigating even the inside of the micro root canal.

The ultrasonic irrigation method is designed to enhance the irrigation effect by injecting a sodium hypochlorite (NaOCl) irrigation solution into the root canal through a very thin bendable needle and by generating the acoustic streaming and bubbles using ultrasonic waves.

However, a size of a bubble generated in a currently widely used instrument is about 100 micrometers to 1 millimeter, which can be construed being significantly large and thus, the irrigation effect may be degraded.

According to Young-Laplace equation, the pressure within a bubble is in an inverse proportion to a size of the bubble. Thus, the smaller the bubble, the larger the explosion pressure of the bubble and thus, micro foreign substances attached to the wall may be easily removed. Accordingly, technology for generating nano-scale bubbles of 1 micrometer or less is required to completely remove foreign substances.

Meanwhile, a device for generating micro or nano-scale bubbles has been developed so far, and a bubble generator using a decompression or a turbulent vortex has been widely employed.

Bubble generation technology using a decompression device refers to generating bubbles during a process of decompressing a super-saturated liquid at a high pressure of 304 kPa to 405 kPa. Bubble generation technology using a turbulent vortex refers to generating bubbles by dropping the pressure within a fluid to be less than or equal to a saturated vapor pressure through the fast spinning vortex flow.

However, the existing technologies are generally employed to generate a large amount of bubbles and to increase dissolved oxygen in, for example, a sewage treatment plant or a water tank. Thus, a corresponding device is relatively large and thus, may not be directly applied to a medical device for the dentist.

Also, a dental scaler is a dental instrument used to remove the tartar attached to the surface of teeth and may include, for example, a passive metal scaler and an ultrasonic scaler.

Here, the ultrasonic scaler may remove foreign substances, for example, the tartar attached to the teeth and around the teeth by spraying a fluid, such as the water or the air, and by generating ultrasonic vibrations at a scaler tip.

SUMMARY

An aspect of the present invention provides a nano bubble generator for irrigating a root canal of a tooth that may spray nano-scale bubbles using a generator configured to generate nano-scale bubbles within a fluid and an ultrasonic portion configured to apply ultrasonic waves to the fluid.

Another aspect of the present invention also provides a dental device that includes a nano bubble generator for irrigating a root canal of a tooth in a handpiece.

According to an aspect of the present invention, there is provided a nano bubble generator for irrigating a root canal of a tooth, the nano bubble generator including: a generator configured to generate nano-scale bubbles within a fluid; a nozzle connected to the generator and configured to move the fluid containing bubbles that flows in from the generator and to apply the fluid at the end of the nozzle; and an ultrasonic portion disposed in the nozzle and configured to apply ultrasonic waves to the fluid containing the bubbles so that the bubbles are maintained in a distributed form.

The generator may be a porous material.

The nozzle may include: a converger connected to the generator and having a decreasing cross-sectional area along a flow direction of the fluid to accelerate the fluid containing the bubbles that flows in from the generator; and a diffuser extended from the converger and having an increasing cross-sectional area along the flow direction of the fluid to decelerate the fluid containing the bubbles that flows in from the converger.

The ultrasonic portion may include: a piezoelectric element configured to vibrate in response to an application of voltage and to generate the ultrasonic waves; and a power source configured to apply the voltage to the piezoelectric element.

According to another aspect of the present invention, there is provided a dental device, including: a dental tip configured to discharge an irrigation solution capable of irrigating a root canal; a handpiece coupled with the dental tip at the end of the handpiece and including a fluid path through which a fluid is conveyed to the dental tip; and a body configured to supply the fluid to the handpiece. Here, the handpiece may include: a generator provided to the fluid path and configured to generate nano-scale bubbles within the fluid; a nozzle connected to the generator and configured to move the fluid containing bubbles that flows in from the generator and to convey the fluid to the dental tip; and an ultrasonic portion disposed in the nozzle to generate ultrasonic vibrations and to apply ultrasonic waves to the fluid containing the bubbles so that the bubbles are maintained in a distributed form.

The ultrasonic portion may convey the ultrasonic vibrations to the dental tip.

EFFECTS

According to embodiments of the present invention, a nano bubble generator for irrigating a root canal of a tooth may spray nano-scale bubbles using a generator configured to generate nano-scale bubbles within a fluid, a nozzle configured to move the fluid containing bubbles and to apply the fluid at the end of the nozzle, and an ultrasonic portion configured to apply ultrasonic waves to the fluid.

Also, the nano bubble generator may generate nano scale bubbles within the fluid using the generator of a porous material.

Also, the nano bubble generator may stably spray bubbles using a converger having a decreasing cross-sectional area along a flow direction of the fluid to accelerate the fluid containing bubbles and a diffuser having an increasing cross-sectional area along the flow direction of the fluid to decelerate the fluid containing bubbles.

Also, the nano bubble generator may maintain the bubbles to be in a distributed state by applying ultrasonic waves using a piezoelectric element and a power source.

BRIEF DESCRIPTION OF THE DRAWINGS

These and/or other aspects, features, and advantages of the invention will become apparent and more readily appreciated from the following description of embodiments, taken in conjunction with the accompanying drawings of which.

DETAILED DESCRIPTION

Reference will now be made in detail to embodiments of the present invention, examples of which are illustrated in the accompanying drawings, wherein like reference numerals refer to like elements throughout. Embodiments are described below to explain the present invention by referring to the figures. However, the present disclosure is not limited to the embodiments and thus, may be differently proposed by adding, modifying, and/or deleting constituent elements of the embodiments, which may also be included in the scope of the invention.

Figure 1:
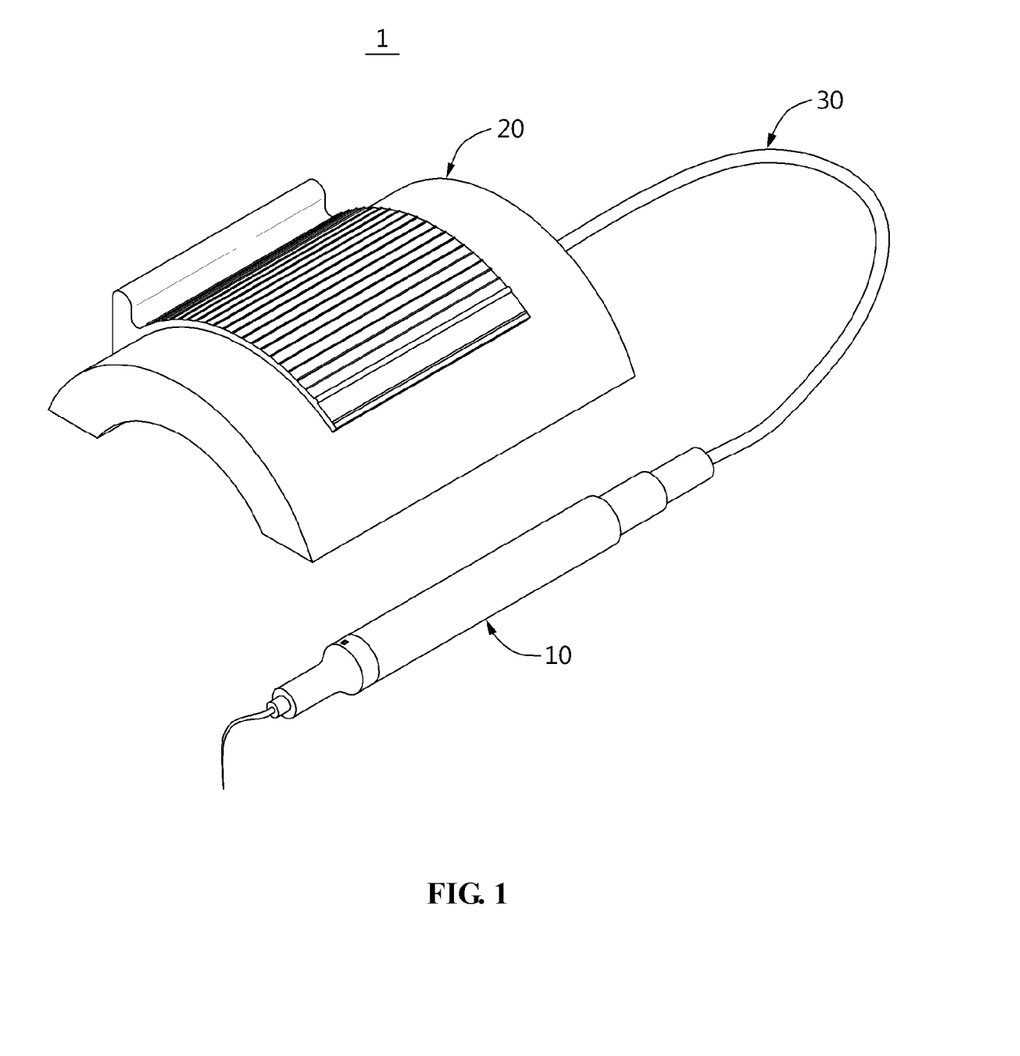
FIG. 1 is a perspective view of a dental device according to an embodiment of the present invention.
Figure 2:
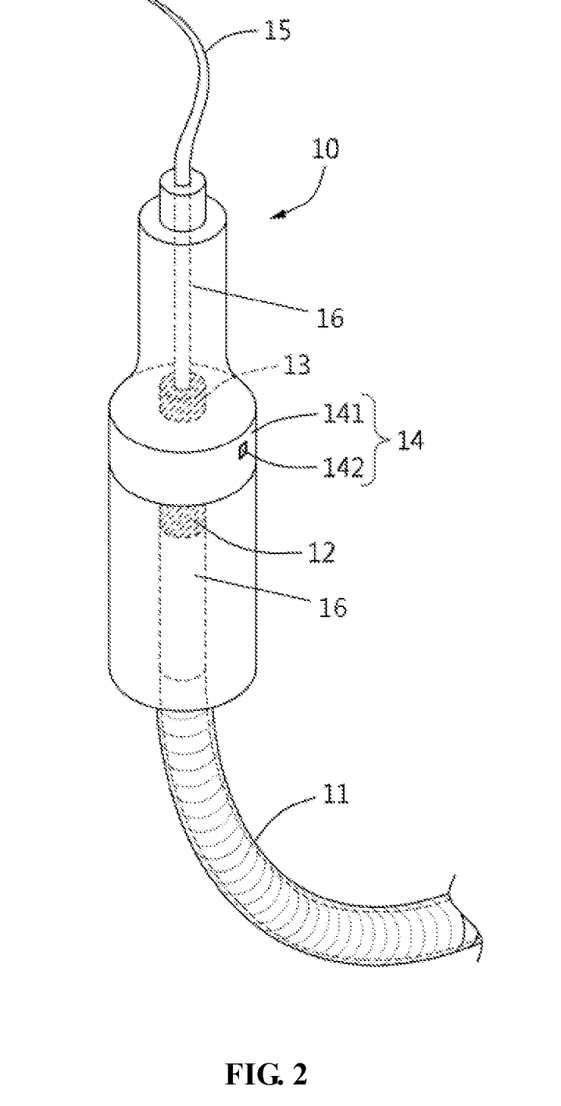
FIG. 2 is a perspective view of a handpiece of a dental device according to an embodiment of the present invention.
Figure 3:
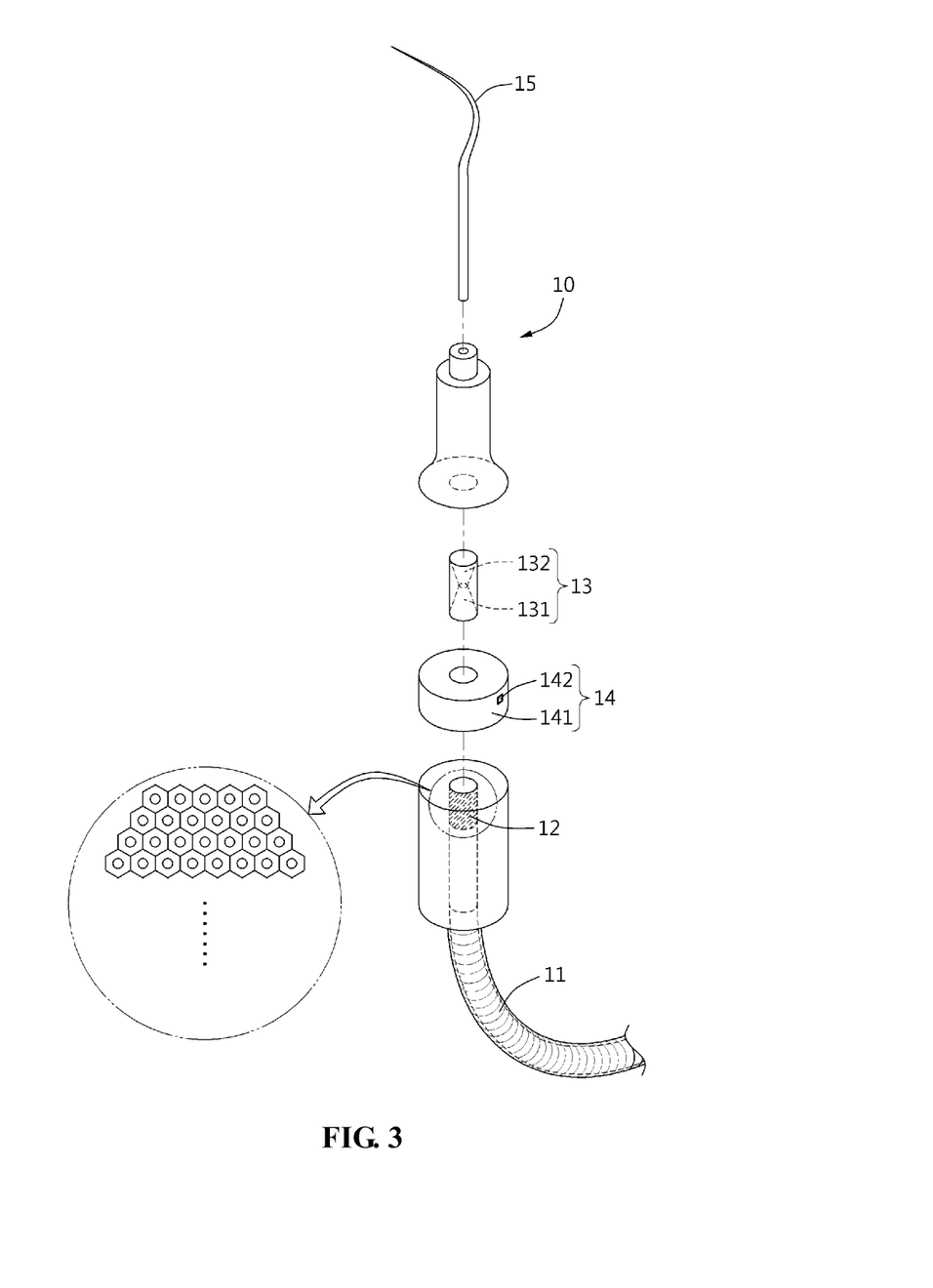
FIG. 3 is an exploded perspective view of a handpiece of a dental device according to an embodiment of the present invention.

FIG. 1 is a perspective view of a dental device 1 according to an embodiment of the present invention, FIG. 2 is a perspective view of a handpiece 10 of the dental device 1 according to an embodiment of the present invention, and FIG. 3 is an exploded perspective view of the handpiece 10 of the dental device 1 according to an embodiment of the present invention.

Referring to FIGS. 1 through 3, the dental device 1 may include the handpiece 10, a dental tip 15, a body 20, and a wire 30.

The handpiece 10 refers to a portion that is grasped by a dentist or a dental hygienist to irrigate the root canal or remove the tartar. The handpiece 10 may be provided in a cylindrical shape that is overall extended to be long, and may also have a smoothly curved surface to be readily grasped by the dentist or the dental hygienist.

A fluid path 16 is provided within the handpiece 10 to supply a fluid, for example, an irrigation solution to be sprayed for irrigating the root canal or removing the tartar. The fluid path 16 may be extended to be long in a lengthwise direction of the handpiece 10, and connected to the dental tip 15 to convey the fluid to the dental tip 15. The fluid path 16 may be formed in a straight-line form to be capable of conveying the supplied fluid to the dental tip 15.

A vibrator (not shown) configured to vibrate the dental tip 15 may be provided to the handpiece 10. The vibrator may be connected to the dental tip 15. The vibrator may generate ultrasonic vibrations within the handpiece 10, and may convey the generated ultrasonic vibrations to the dental tip 15.

Dissimilar thereto, instead of providing the vibrator to the handpiece 10, an ultrasonic portion 14 may be connected to the dental tip 15 to transfer the ultrasonic vibrations to the dental tip 15.

The handpiece 10 may include a nano bubble generator for irrigating a root canal of a tooth configured to generate nano scale bubbles within the fluid flowing through the fluid path 16 and to maintain the generated bubbles to be in a distributed state within the fluid, which will be described later.

The dental tip 15 is provided in an approximately long conical shape having a decreasing width towards a front end. The dental tip 15 may be provided in a reversed "L" shape for easiness of a work, and a discharging hole (not shown) via which the fluid is dischargeable may be formed at the end of the dental tip 15. The dental tip 15 may be detachably coupled at the end of the handpiece 10 and accordingly, the dental tip 15 may be replaced or reused after being disinfected.

The body 20 may supply the fluid, for example, an irrigation solution to the handpiece 10 through a pump. Also, the body 20 may generate ultrasonic signals capable of controlling ultrasonic waves generated by the vibrator or the ultrasonic portion 14, and may transfer the generated ultrasonic signals to the handpiece 10.

The body 20 may be provided in any shape. For example, the body 20 may be manufactured in a portable type to be portable and mobile, and may also be provided within a chair 50 of FIG. 6.

The wire 30 may connect the body 20 and the handpiece 10, and may provide a passage through which the fluid, for example, an irrigation solution is conveyed from the body 20 to the handpiece 10. Also, the wire 30 may transfer ultrasonic signals or electrical energy from the body 20 to the handpiece 10.

Figure 4:
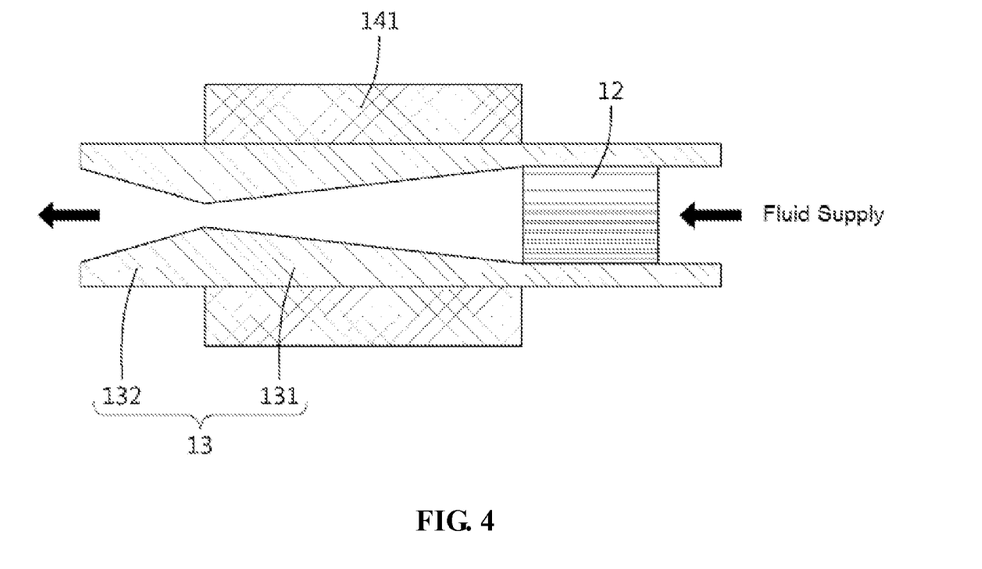
FIG. 4 is a cross-sectional view of a nano bubble generator for irrigating a root canal of a tooth included in a dental device according to an embodiment of the present invention.
Figure 5A:
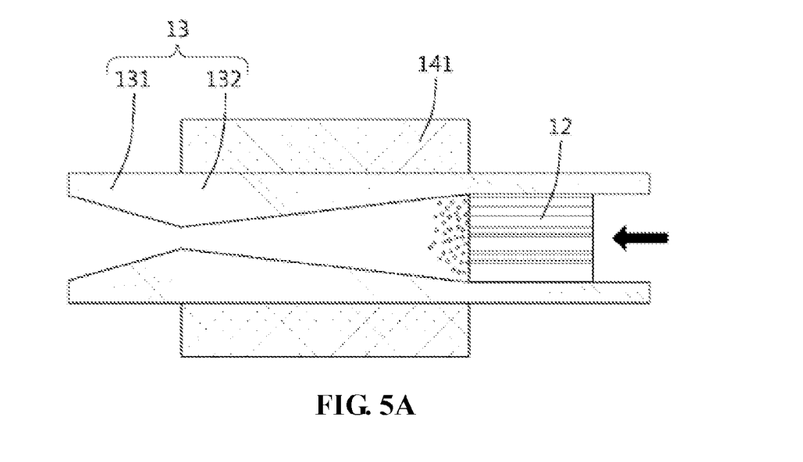
FIG. 5A is a cross-sectional view describing an example in which bubbles are generated within a fluid having passed through a generator of a nano bubble generator for irrigating a root canal of a tooth according to an embodiment of the present invention.
Figure 5B:
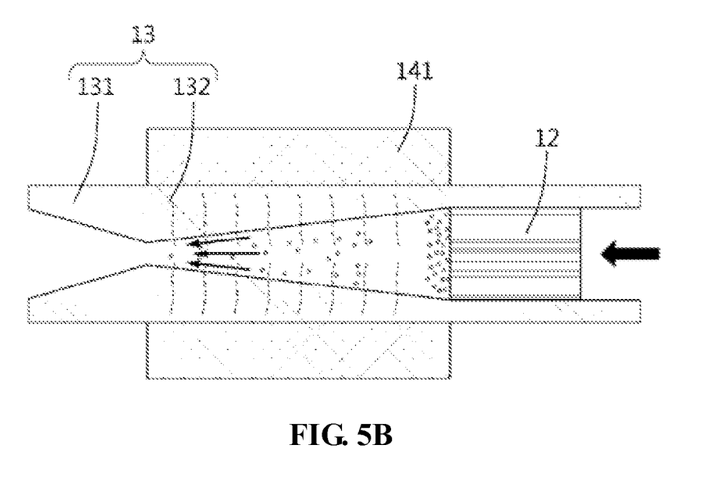
FIG. 5B is a cross-sectional view describing an example in which the bubbles of FIG. 5A pass through a converger of a nozzle of the nano bubble generator and the fluid accelerates in a flow direction in which a cross-sectional area of the converger decreases.
Figure 5C:
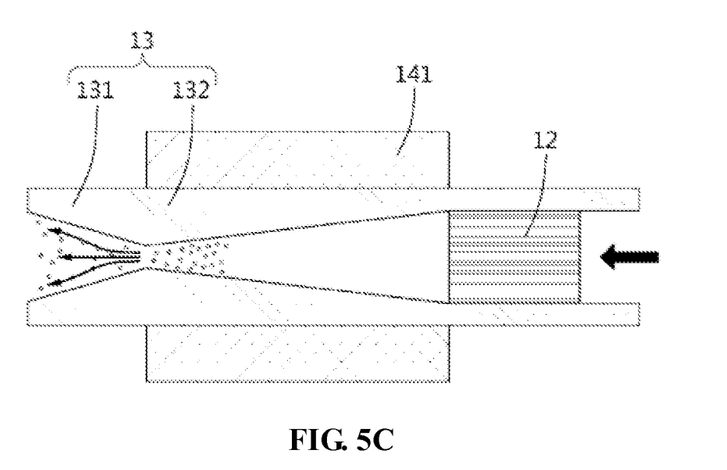
FIG. 5C is a cross-sectional view describing an example in which the accelerated fluid of FIG. 5B sequentially passes through the converger and a diffuser of the nozzle and decelerates in a flow direction in which a cross-sectional area of the diffuser increases.

FIG. 4 is a cross-sectional view of a nano bubble generator for irrigating a root canal of a tooth included in the dental device 1 according to an embodiment of the present invention, FIG. 5A is a cross-sectional view describing an example in which bubbles are generated within a fluid having passed through a generator 12 of the nano bubble generator according to an embodiment of the present invention, FIG. 5B is a cross-sectional view describing an example in which the bubbles of FIG. 5A pass through a converger 131 of a nozzle 13 of the nano bubble generator and the fluid accelerates in a flow direction in which a cross-sectional area of the converger 131 decreases, and FIG. 5C is a cross-sectional view describing an example in which the accelerated fluid of FIG. 5B sequentially passes through the converger 131 and a diffuser 132 of the nozzle 13 and decelerates in a flow direction in which a cross-sectional area of the diffuser 132 increases.

Referring to FIGS. 4 through 5C, the handpiece 10 may include the nano bubble generator configured to generate nano scale bubbles within the fluid flowing in the fluid path 16, and to maintain the generated bubbles to be in a distributed state. The nano bubble generator may include a supply 11, the generator 12, and the nozzle 13.

The supply 11 may supply the fluid to the generator 12. Here, a NaOCl irrigation solution generally used for a dental irrigation solution may be used for the fluid. However, the present invention is not limited thereto and thus, various types of fluids may be supplied. Also, the supply 11 may supply the pressurized saturated fluid so that the generator 12 may generate bubbles within the fluid. A separate process of processing the fluid to be in a saturated state may be required. The supply 11 may pressurize the fluid saturated through the separate process using, for example, a pump, and may supply the pressurized saturated fluid to the generator 12.

The supply 11 may be provided in a shape of a tube in which an empty space is formed to flow the fluid, and may be formed of a flexible material. For example, the supply 11 may be formed as a flexible hose using a metal material. The supply 11 may be connected to the wire 30, and may be supplied from the wire 30 with the fluid, for example, an irrigation solution supplied from the body 20.

The generator 12 may be formed along the fluid path 16 provided within the handpiece 10, and may be connected to the supply 11 to generate bubbles within the fluid supplied from the supply 11.

Also, the generator 12 may be provided using a porous material in an external shape of a membrane formed as a significantly thin film of about 0.5 mm to about 1.2 mm and pores in a cylindrical shape.

The generator 12 may use aluminum or a silicone material, however, the present invention is not limited thereto. A pore of a porous material may have a size of about 1 nanometer to about 5 micrometers to generate nano-scale bubbles.

The porous material may be produced using an electrochemical anodization method. The electrochemical anodization method refers to a method of producing the porous material using a power supply device, an electrochemical cell, and a voltage (current) control device. In addition, the electrochemical anodization method produces the porous material with a relatively simple configuration, and also controls a pore size with a relatively high repeatability and thus, may be significantly useful in producing the porous material.

When the pressurized saturated fluid supplied from the supply 11 to the generator 12 passes through the generator 12, Bernoulli's equation states that an increase in the speed of the fluid occurs simultaneously with a significant decrease in pressure. When the pressure is dropped down to a saturated vapor pressure, the vapor dissolved within the fluid may gather to generate bubbles. Since a pore of the porous material has a nano-scale, a generated bubble may also have a nano-scale. Accordingly, the generator 12 may function to generate nano-scale bubbles within the fluid.

The nozzle 13 may be provided within the handpiece 10. The nozzle 13 may be connected to one side of the generator 12 within the handpiece 10, and may move the fluid containing bubbles that flows in from the generator 12 and thereby spray the fluid at the end of the nozzle 13. The sprayed fluid may move along the fluid path 16 formed within the handpiece 10, and may be conveyed to the dental tip 15 coupled at the end of the handpiece 10.

The nozzle 13 may include the converger 131 having a decreasing cross-sectional area along the flow direction of the fluid and the diffuser 132 having an increasing cross-sectional area along the flow direction of the fluid. In the converger 131, the pressure of the fluid may decrease as the cross-sectional area gradually decreases in a direction in which the fluid flows, and the fluid containing bubbles that flows in from the generator 12 may accelerate. Also, in the diffuser 132, the pressure of the fluid may increase as the cross-sectional area gradually increases in the direction in which the fluid flows, and the fluid containing bubbles that flows in through the converger 131 may decelerate.

The converger 131 of the nozzle 13 may be formed to have a length greater than a length of the diffuser 132. A space formed on a boundary between the converger 131 and the diffuser 132 may be formed to have a smallest diameter over the nozzle 13.

The ultrasonic portion 14 may include a piezoelectric element 141 and a power source 142. The power source 142 may apply voltage to the piezoelectric element 141. In response thereto, the piezoelectric element 141 provided to surround the converger 131 of the nozzle 13 may apply ultrasonic waves to the fluid containing the bubbles within the converger 131, so that the bubbles may be maintained to be in a distributed state. Here, the piezoelectric element 141 may be positioned at the middle of the handpiece 10, and may be provided in a donut shape to surround a portion of the nozzle 13, thereby driving ultrasonic vibration energy.

In detail, the ultrasonic portion 14 may reduce sizes of bubbles to be smaller by applying, to the bubbles contained within the fluid, the ultrasonic vibration energy occurring in response to the voltage applied to the piezoelectric element 141 and thereby vibrating the bubbles.

A piezoelectric phenomenon by the piezoelectric element 141 may refer to an energy conversion, for example, a conversion between mechanical energy and electrical energy using a permanent dipole that has occurred due to the asymmetry of crystal of the piezoelectric element 141. That is, the piezoelectric phenomenon refers to a phenomenon that the electrical energy occurs when applying the mechanical energy to the piezoelectric element 141, and, conversely, the mechanical energy occurs when applying the electrical energy to the piezoelectric element 141. Also, when unique vibrations occur on the crystal of the piezoelectric element 141 and when elastic vibrations and electrical vibrations match, further strong vibrations may occur through coupling with piezoelectricity.

The piezoelectric element 141 may use a polycrystalline material generally used for an ultrasonic vibrator. For example, the piezoelectric element 141 may use lead zirconate titante (PZT) base, PZT-complex perovskite base, barium titanate ($BaTiO_3$), monoammonium phosphate ($NH_4H_2PO_4$), and tartaric acid ethylenediamine. However, the present invention is not limited thereto and thus, a variety of materials may be used for the piezoelectric element 141.

Ultrasonic waves may be generated using the piezoelectric element 141 and the power source 142, by applying the voltage, for example, the electrical energy to the piezoelectric element 141 to thereby vibrate the piezoelectric element 141, for example, to generate the mechanical energy.

In addition to the aforementioned piezo method, ultrasonic waves may be generated through a magnetostriction oscillation method using a phenomenon that a metal is dented when the metal is magnetized. The range of ultrasonic waves obtainable through the magnetostriction oscillation method may reach a maximum of about 20 billion Hertz (Hz).

Accordingly, bubbles within the fluid may be distributed without being merged using the ultrasonic portion 14.

The ultrasonic portion 14 may function to reduce sizes of bubbles within the fluid to be smaller by exciting the bubbles within the fluid, and may be connected to the dental tip 15 to convey the vibration energy to the dental tip 15. In detail, the ultrasonic portion 14 may also perform the functionality of the vibrator and in this case, the vibrator may not be separately provided.

The nozzle 13 may include the converger 131 and a diffuser 132 that are divided in the flow direction of the fluid.

The converger 131 may be provided to have the decreasing cross-sectional area along the flow direction of the fluid in order to accelerate the fluid, and the diffuser 132 may be provided to have the increasing cross-sectional area along the flow direction of the fluid in order to decelerate the fluid.

The converger 131 may be connected to the generator 12 and may provide a space in which the fluid having passed through the generator 12 and containing bubbles flows. Also, to prevent merging between the bubbles contained within the fluid having passed through the generator 12, the fluid path 16 having a decreasing cross-sectional area in the flow direction of the fluid may be formed to accelerate the fluid.

The diffuser 132 may be extended from the converger 131 and may provide a space in which the fluid having passed through the converger 131 and containing bubbles flows and is sprayed at the end of the nozzle 13. Also, to stabilize the bubbles contained within the fluid having passed through the converger 131, the fluid path 16 having an increasing cross-sectional area in the flow direction of the fluid may be formed to decelerate the fluid.

As described above, using the converger 131 and the diffuser 132 of the nozzle 13, the bubbles contained within the fluid may be stably sprayed without being merged.

That is, using the generator 12, the nozzle 13, and the ultrasonic portion 14 included in the dental device 1 according to an embodiment of the present invention, it is possible to stably generate nano bubbles and to spray the nano bubbles towards the root canal.

Hereinafter, a process of generating nano bubbles using the nano bubble generator included in the dental device 1 according to an embodiment of the present invention will be described with reference to FIGS. 5A, 5B, and 5C.

Referring to FIG. 5A, the pressurized saturated fluid that has been supplied from the supply 11 may pass through the generator 12. During a process in which the fluid passes through the generator 12, the speed of the fluid increases and the pressure significantly decreases up to the saturated vapor pressure according to Bernoulli's equation. In this case, a cavitation that the vapor dissolved within the fluid gathers to generate bubbles may occur. Since a pore of the generator 12 has a nano-scale, a bubble generated by the cavitation may have a nano-scale.

The cavitation refers to the formation of vapor cavities in a liquid caused by a decreasing pressure applied to the liquid, that is, the wave energy and thus, numerous bubbles may be generated. In this case, the significantly great pressure may occur until the cavities are collapsed. The bubbles generated as above are very unstable and thus, when the bubbles pass through the generator 12 to be conveyed to the converger 131, sizes of bubbles may increase due to merging between the bubbles or may be collapsed due to an increase in the pressure.

Referring to FIG. 5B, when the fluid passes through the converger 131, voltage may be applied from the power source 142 to the piezoelectric element 141 provided to surround the converger 131. In response thereto, the piezoelectric element 141 may apply ultrasonic waves to the fluid and prevent the bubbles from being merged.

Also, the converger 131 is provided to have the decreasing cross-sectional area along the flow direction of the fluid. Thus, while the fluid is passing through the converger 131, the pressure may gradually decrease and the bubbles may reach the diffuser 132 without being merged or collapsed.

Referring to FIG. 5C, the fluid may reach the diffuser 132 and the diffuser 132 is provided to have the increasing cross-sectional area along the flow direction of the fluid. Thus, while the fluid is passing through the diffuser 132, the pressure may gradually increase and the distributed bubbles may be further reduced and stabilized. The stably generated nano bubbles may be sprayed at the end of the nozzle 13 together with the fluid.

Through the overall operation of the dental device 1 according to an embodiment of the present invention, nano bubbles may be stably generated and sprayed.

In detail, the pressurized saturated fluid may be supplied from the supply 11 to the generator 12. While the supplied fluid passes through the generator 12, bubbles may be generated within the fluid.

When the fluid containing bubbles passes through the converger 131, the fluid may accelerate and at the same time, the pressure may decrease, thereby preventing the bubbles from being merged.

Further, the bubbles may be prevented from being merged by applying ultrasonic waves to the fluid using the ultrasonic portion 14 provided to the converger 13 and thereby distributing the bubbles. The fluid having passed through the converger 131 may decelerate while passing through the diffuser 132 and at the same time, the pressure may increase, thereby stably conveying the bubbles to the dental tip 15 disposed at the end of the handpiece 10, through the fluid path 16 provided within the handpiece 10 at the end of the diffuser 132.

As described above, the dental device 1 according to an embodiment of the present invention may convey the fluid to the dental tip 15 coupled at the end of the handpiece 10 and may spray nano-scale bubbles using the generator 12 configured to generate the nano-scale bubbles within the fluid, the nozzle 13 configured to flow the fluid containing bubbles and spray the fluid at the end of the nozzle 13, and the ultrasonic portion 14 configured to apply ultrasonic vibration energy to the fluid.

Figure 6:
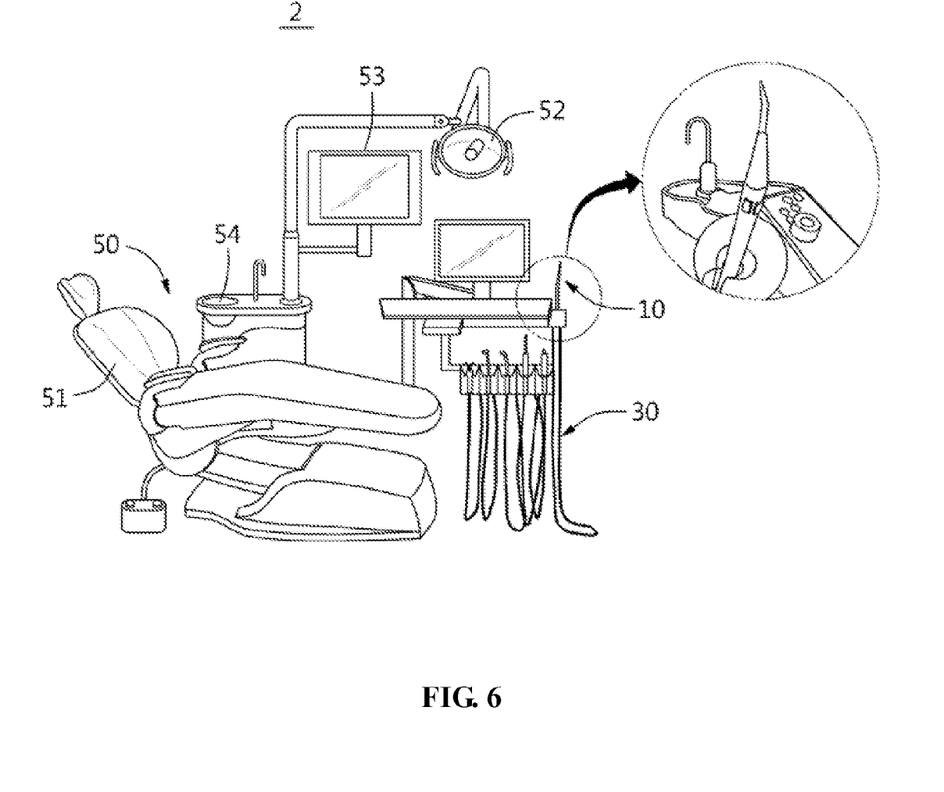
FIG. 6 illustrates a dental device according to another embodiment of the present invention.

FIG. 6 is a perspective view of a dental device 2 according to another embodiment of the present invention.

Referring to FIG. 6, the dental device 2 may include a handpiece 10, a wire 30, and a unit chair 50.

The unit chair 50 may include a chair 51 on which a patient may lie down or sit down, a lighting 52 capable of emitting light towards the inside of a mouth of the patient, a display 53 configured to display a state of the patient, for example, an X-ray photo, and a sink 54 at which the patient may rinse the mouth after treatment.

The dental device 1 of FIG. 1 is provided in a portable and mobile type, whereas the dental device 2 of FIG. 6 is provided in an immobile type and is installed in a dental clinic. In this regard, the dental device 2 of FIG. 6 may differ from the dental device 1 of FIG. 1, however, may have the same configuration as the dental device 1 of FIG. 1 in which the fluid path 16 via which the fluid, for example, an irrigation solution may flow is provided within the handpiece 10, nano-scale bubbles are generated within the fluid flowing in the fluid path 16, and ultrasonic waves are applied to maintain the bubbles to be in a distributed state. Accordingly, a further description related thereto will be omitted here.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. A nano bubble generator for irrigating a root canal of a tooth, the nano bubble generator comprising:
    a generator configured to generate nano-scale bubbles within a fluid;
    a nozzle connected to the generator and configured to move the fluid containing bubbles that flows in from the generator and to apply the fluid at the end of the nozzle; and
    an ultrasonic portion disposed in the nozzle and configured to apply ultrasonic waves to the fluid containing the bubbles so that the bubbles are maintained in a distributed form,
    wherein the nozzle comprises:
        a converger connected to the generator and having a decreasing cross-sectional area along a flow direction of the fluid to accelerate the fluid containing the bubbles that flows in from the generator; and
        a diffuser extended from the converger and having an increasing cross-sectional area along the flow direction of the fluid to decelerate the fluid containing the bubbles that flows in from the converger.

2. The nano bubble generator of claim 1, wherein the generator is a porous material.

3. The nano bubble generator of claim 1, wherein the ultrasonic portion comprises:
    a piezoelectric element configured to vibrate in response to an application of voltage and to generate the ultrasonic waves; and
    a power source configured to apply the voltage to the piezoelectric element.

4. A dental device, comprising:
    a dental tip configured to discharge an irrigation solution capable of irrigating a root canal;
    a handpiece coupled with the dental tip at the end of the handpiece and comprising a fluid path through which a fluid is conveyed to the dental tip; and
    a body configured to supply the fluid to the handpiece,
    wherein the handpiece comprises:
        a generator provided to the fluid path and configured to generate nano-scale bubbles within the fluid;
        a nozzle connected to the generator and configured to move the fluid containing bubbles that flows in from the generator and to convey the fluid to the dental tip; and
        an ultrasonic portion disposed in the nozzle and configured to generate ultrasonic vibrations and to apply ultrasonic waves to the fluid containing the bubbles so that the bubbles are maintained in a distributed form,
    wherein the nozzle comprises:
        a converger connected to the generator and having a decreasing cross-sectional area along a flow direction of the fluid to accelerate the fluid containing the bubbles that flows in from the generator; and
        a diffuser extended from the converger and having an increasing cross-sectional area along the flow direction of the fluid to decelerate the fluid containing the bubbles that flows in from the converger.

5. The dental device of claim 4, wherein the ultrasonic portion is configured to convey the ultrasonic vibrations to the dental tip.

* * * * *